(12) United States Patent
Fuhr et al.

(10) Patent No.: US 6,801,311 B1
(45) Date of Patent: Oct. 5, 2004

(54) PROCESS AND DEVICE FOR THE DETECTION OF MICROSCOPICALLY SMALL OBJECTS

(75) Inventors: Günter Fuhr, Berlin (DE); Thomas Schnelle, Berlin (DE); Christoph Reichle, Berlin (DE); Henning Glasser, Berlin (DE); Torsten Müller, Berlin (DE)

(73) Assignee: Evotec Technologies GmbH, Duesseldorf (DE)

( * ) Notice: Subject to any disclaimer, the term of this patent is extended or adjusted under 35 U.S.C. 154(b) by 0 days.

(21) Appl. No.: 09/889,908
(22) PCT Filed: Jan. 26, 2000
(86) PCT No.: PCT/EP00/00621
§ 371 (c)(1),
(2), (4) Date: Dec. 12, 2001
(87) PCT Pub. No.: WO00/45147
PCT Pub. Date: Aug. 3, 2000

(30) Foreign Application Priority Data

Jan. 26, 1999 (DE) ......................................... 199 03 001

(51) Int. Cl.⁷ .............................................. G01N 15/02
(52) U.S. Cl. ....................................................... 356/336
(58) Field of Search ................................ 356/335, 336, 356/337, 338, 341, 343, 904

(56) References Cited

U.S. PATENT DOCUMENTS

| | | | |
|---|---|---|---|
| 3,563,660 A | | 2/1971 | Soloway et al. |
| 5,644,388 A | * | 7/1997 | Maekawa et al. .............. 356/73 |
| 5,654,797 A | | 8/1997 | Moreau et al. |
| 5,684,587 A | | 11/1997 | Naqwi |
| 5,798,827 A | * | 8/1998 | Frank et al. ................... 356/39 |
| 5,815,265 A | | 9/1998 | Molter et al. |
| 2002/0003625 A1 | * | 1/2002 | Hansen et al. .............. 356/338 |

FOREIGN PATENT DOCUMENTS

| | | |
|---|---|---|
| DE | 196 28 156 | 1/1998 |
| DE | 197 23 873 | 12/1998 |
| WO | WO 98/29732 | 7/1998 |

OTHER PUBLICATIONS

Fuhr, Günter et al., "Radio–Frequency Microtools for Particle and Live Cell Manipulation"; "*Naturwissenschaften*", 1994, pp. 528–535, vol. 81.

* cited by examiner

*Primary Examiner*—Rodney Fuller
(74) *Attorney, Agent, or Firm*—Caesar, Rivise, Bernstein, Cohen & Pokotilow, Ltd.

(57) ABSTRACT

For object detection, particularly in fluidic microsystems, optical imaging of at least one resting or moving object (10) on a structured mask (20) with at least one segment from a flat section (80), in which the object (10) is located at least partially or temporarily and which has a characteristic dimension smaller than the dimension of the object (10) or its movement path, to a detector unit, detection of the quantity of light transmitted by the structured mask (20), and generation of a detector signal which has a predetermined relationship with the quantity of light, and evaluation of the detector signal in regard to the presence of the object (10), its position, its shape and/or the temporal change of the position are performed.

20 Claims, 18 Drawing Sheets

PROCESS AND DEVICE FOR THE DETECTION OF MICROSCOPICALLY SMALL OBJECTS

BACKGROUND OF THE INVENTION

The invention concerns a process and a device for the detection of microscopically small objects, particularly for the detection of the presence and/or for the measurement of the location and/or the change in location of the objects, for example in fluidic microsystems. The microscopically small objects are particularly synthetic or biological particles which are manipulated in a fluidic microsystem. The invention also concerns uses of the process and/or the device, particularly for object detection depending on mechanical, electrical, or chemical interactions of the objects with their environment or other objects.

Using fluidic Microsystems for particle-specific manipulation of microscopically small objects under the effect of hydrodynamic and/or electrical forces is generally known. The manipulation of biological particles in microsystems with high frequency electric fields on the basis of negative dielectrophoresis is, for example, described by G. Fuhr et al. in "Naturwissenschaften", vol. 81, 1994, p. 528 et seq. The manipulation of the objects comprises, among other things, sorting according to specific characteristics, alteration of the object under the effect of electrical fields (e.g. cell poration), chemical treatment, mutual bringing together and interaction of the objects and similar actions. The provision of predetermined hydrodynamic and/or electrical forces is performed through the design of the channel structure of the microsystem and/or the geometric shapes of microelectrodes for forming high frequency electric fields and their control.

The previously known Microsystems do allow monitoring of the object manipulation occurring with optical means, e.g. using a microscope with a camera. This optical monitoring has, however, been restricted until now to visual examinations or the use of costly image recognition processes for processing the camera image. The image processing processes are, however, significantly too slow for the object speeds which arise, if real-time monitoring is to be practiced. Therefore, until now the implementation of automatic system controls, in which, for example, specific process variations occur depending on location, movement state, or number of objects observed, has been excluded.

A process for movement detection of microscopic objects which perform an at least partially periodic movement is known from PCT/EP97/07218. This process is based on the use of a Fourier analysis of a detector signal which characterizes the object movement over multiple movement periods. This process represents a significant simplification relative to the use of computer-aided image processing processes, but it is restricted to applications with periodic movements. In general, however, non-periodic movements or rest conditions of the objects also occur in a microsystem, the detection of which, particularly for automatic control of a microsystem, is also of interest.

Detecting the presence of small particles in suspensions on the basis of scattered light measurements is also known. However, this principle can only be realized with multiple particles, and can therefore not be particle-specific. In addition, no information on the movement state of particles (location, speed, or similar parameters) can be derived. It is the object of the invention to indicate an improved process for object detection which can be used in any desired movement or rest state of the objects to be detected and which allows rapid and reliable signal evaluation. The object of the invention is also to indicate devices for implementing such a process and new applications of the object detection according to the invention.

SUMMARY OF THE INVENTION

The invention is based on the idea of imaging the locational area (movement path or position) of the object to be detected enlarged on a mask which is set up in at least one segment for transmitting (reflection or transmission) of the light from one part of the locational area (so-called section) and otherwise for suppressing of transmission outside the segment. The at least one light-transmitting segment of the mask has a characteristic dimension which is smaller than the image of the entire object or the lateral extension of the movement path of the object. The quantities of light of the object image transmitted by the mask are summarily imaged on a detector device, at which a detector signal is generated having a predetermined relationship with the quantity of light detected and allowing an evaluation in regard to the presence of the object, its position, and/or the temporal change of the position. The quantity of light detected by the detector device is modulated in a characteristic way by the masked image of a section of the object and/or of the object path. The time dependence of the detector signal, particularly the temporal position of signal maxima, the amplitudes of the signal maxima, and the temporal amplitude shape in the vicinity of the signal maxima provides information not only on the location and the speed of the objects, but also on derived dimensions such as the frequency of periodic movements, quantitative information on particle numbers, movement direction, centering in the Microsystems, or similar dimensions.

One subject of the invention is therefore particularly object detection on the basis of a diaphragma measurement principle, in which a summary detection of the quantities of light coming out of a section of the object or the object path occurs. Correspondingly, the partial object imaging can, in principle, occur on a diaphragma (screen) with suitable dimension. In the simplest case, the mask consists of an element opaque to light with a round or angular opening which is suitably dimensioned for realization of the partial image of the object to be detected according to the invention.

However, corresponding to preferred embodiments of the invention, the mask has a segmentation with a predetermined geometry. The at least one segment for transmission of the light of the partial image has a geometric shape which is selected, depending on the application, according to the respective object movements (e.g. translation, rotation, translational vibration, rotational vibration, or similar movements) expected at the measurement point.

According to the invention, an enlarged image of the locational area of the objects to be detected (e.g. in a microsystem) is preferably provided on the mask. For this purpose, the segmentation of the mask, which is set up for transmission of the light from a partial image, can be absolutely larger than the section or part of the object concerned. This is advantageous for the production and justification of the mask.

Preferred applications of object detection according to the invention are provided in fluidic microsystems, particularly in automatic regulation of system functions, in dielectric single particle spectroscopy, and in the examination of interactions between objects and other objects and/or substrates. Objects detected according to the invention have a characteristic diameter in the range below 500 μm down to the 100 nm range and comprise synthetic or biological particles (or particle aggregates). The synthetic particles are, for example, membrane-enclosed formations, such as liposomes or vesicles, or plastic particles (so-called beads). The biological particles are biological cells or cell aggregates or cell components, microorganisms, viruses, or similar objects.

One subject of the invention is also a device for implementation of object detection according to the invention, comprising an optical imaging unit for imaging a part of an object to be detected (or of its path) via a mask on a detector unit, which generates a detector signal in a specific relationship with the quantity of light detected, and an evaluation unit for determining characteristics of the movement or rest state of the object. The imaging unit contains, in particular, the mask, on which the object or its movement path is imaged in enlarged form and which only transmits a section of the image to the detector unit. According to a preferred embodiment of the invention, which is explained in detail below, the mask is a screen with a predetermined transmission geometry. The invention is, however, not restricted to this design, but can also be implemented with other mask designs which are set up to fulfill the same function as the transmitting screen. Instead of a transparent segment in an opaque mask material, an opaque segment (with the same geometry as the previously mentioned transparent segment) can be used as the mask in an otherwise transparent environment. Correspondingly, a reflection principle can be realized instead of the transmission principle.

The imaging unit is preferably part of a microscope arrangement, which is known per se, containing the mask for generating the partial image in the beam path. In this way, visual object observation can occur simultaneously with object detection. The combination with the microscope arrangement is, however, not urgently necessary. Particularly for automatic applications, the imaging unit can be provided directly in a microsystem.

The invention has the following advantages. The object detection according to the invention does not require imaging processing processes which are costly in measurement and time. It allows highly precise measurement with imaging and measurement units which are available per se. An existing microscope assembly can be set up for object detection according to the invention simply by attaching the mask mentioned. The mask segmentation according to the invention allows object detection without a large amount of adjustment. The object detection can be automated easily. Particular advantages result in the combination of mask-based detection with dielectric single particle spectroscopy for highly precise determination of dielectric particle characteristics from the movement characteristics of the particles in high frequency electric fields. Through the use of predetermined mask types, a device according to the invention can be adjusted without problems for the detection of greatly varying types of movement, without having to resort to image processing methods or having to perform a modification of the system. It is sufficient for a detector unit to contain one single detector whose measurement signals can be serially processed. This allows processing in real time, which is particularly significant for switching and sorting applications in microsystems.

A further advantage of the invention arises from the geometric mask structuring. In contrast to the typical "pinhole" measurement principle, the mask segments are designed as smaller than the image of the entire object, but, unlike apertures (as they are known in, for example, confocal microscopy), are implemented as planar. In this way, increased functional reliability is achieved, even with deviations of the objects from the expected movement paths which occur in practice. The mask segmentation allows for compensation of tolerances as the object moves.

BRIEF DESCRIPTION OF SEVERAL VIEWS OF THE DRAWINGS

Further characteristics and advantages of the invention are described in the following with reference to the attached drawings. These show.

DETAILED DESCRIPTION OF THE INVENTION

The invention will be described in the following with the example of fluidic Microsystems for the manipulation of synthetic or biological particles. The realization of the invention is not bound to specific particle types. However, it is necessary for specific applications that the particles have a surface structure which can be imaged (e.g. structures on biological cells). If this is not initially present, however, the particles can also be provided with structuring (e.g. with a fluorescence marking). The microsystems have a channel structure with typical transverse dimensions in the $\mu$m range and typical lengthwise dimensions in the mm range. Microelectrodes having predetermined electrode shapes and arrangements, which are set up to have high frequency voltages (frequencies in the kHz to MHz range, amplitudes in the mV to V range) applied to them in order to subject the particles flowing or resting in a suspension in the channels to electric fields, are affixed to the channel walls. Under the effect of the electric fields, a predetermined force is exercised on the particles on the basis of negative or positive dielectrophoresis. Further particulars of these fluidic microsystems are known per se and are therefore not described in the following. Furthermore, it is to be emphasized that the invention is not restricted to fluidic Microsystems, but can also be realized in other applications in which individual objects, particularly microscopically small objects, are to be detected, specifically in regard to their presence, their position, and their speed.

Figure 1A:
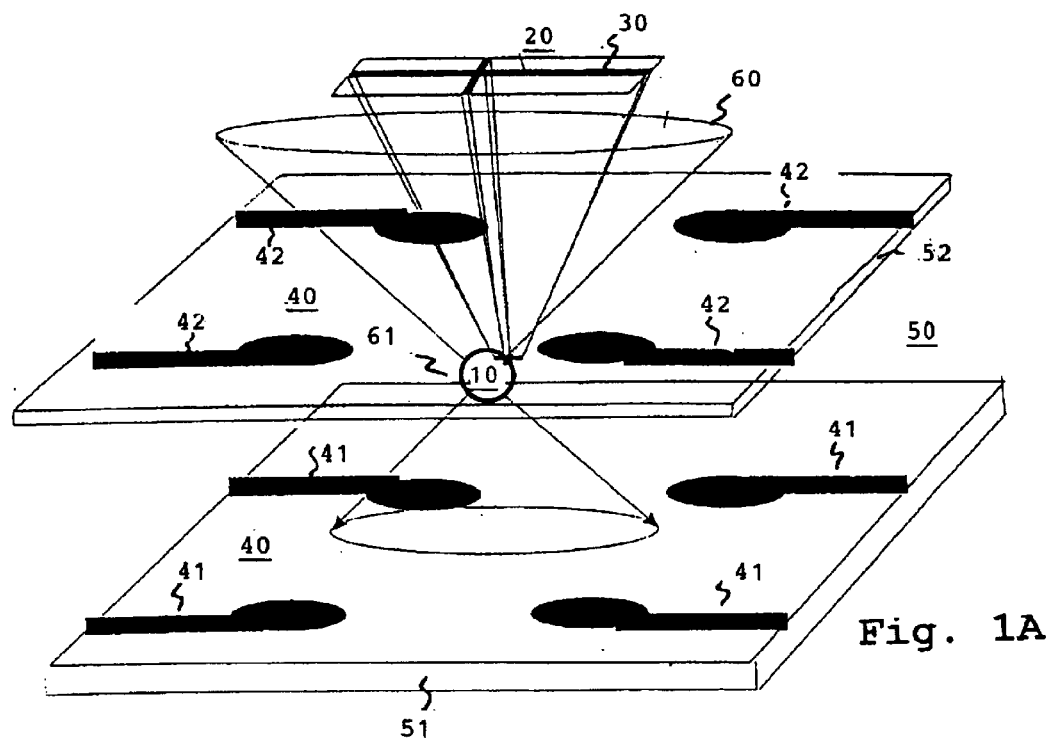
FIGS. 1A, 1B a schematic perspective view of a microelectrode arrangement for illustration of the detection principle according to the invention in the example of a first mask shape, FIGS. 2 to 12, schematic top views of microelectrode arrangements for illustration of further mask shapes, with characteristic traces of the detector signals being illustrated in the lower part of the figures, FIGS. 13A, 13B to 15 schematic perspective views of microelectrode arrangements for illustration of the investigation of interactions between a test object and a substrate or another object, FIGS. 16 to 18 schematic perspective views of microelectrode arrangements for illustration of a force or field measurement in the microsystem, and FIG. 19 a block diagram of an exemplary embodiment of the detector unit according to the invention.

FIG. 1A shows a schematic perspective view of a section of a microsystem with a channel 50, with only the channel bottom 51 and the channel cover 52 illustrated, which, for example, can have a particle suspension flow through it (from the front to the rear in the illustration). The electrode arrangement 40 is an octopole arrangement, with four microelectrodes 41 on the channel bottom 51 and four microelectrodes 42 on the channel cover 52. A rotating electrical field (rotational field) is generated with the electrode arrangement 40 in a way a which is known per se, with the particle 10 being held in its center in the focus 61 of a trapping laser 60. The trapping laser 60 is part of a so-called optical tweezer (or laser tweezer), as it is known per se.

At least one wall of the channel 50 (e.g. the channel cover 52) is optically transparent. An imaging unit according to the invention is provided, on the side of the transparent channel wall having a thickness less than or equal to 250 μm, which is intended for imaging a section 80 of the locational area of the particle 10 (in this case the center of the electrode arrangement 40) on a detector unit. The essential element of the imaging unit, which is otherwise not illustrated, is the mask 20 in the form of an essentially flat screen with a predetermined geometric transmission shape. In the example illustrated, the transmission shape is in the form of crossing strips. The strips form the segments 30 of the mask 20. In general, the segments of the mask according to the invention are preferably positioned flat or two-dimensionally in order to obtain the information on the location of the particles and/or the changes in location.

The locational area of the particle 10, and therefore also the section 80 and/or a part of the section 10, are imaged with optical elements (not shown) on the plane of the mask 20. The mask 20 transmits a part of the light forming the image of the particle 10 to the detector (also not shown). If the location of the particle 10 in the microsystem changes, the light summarily captured at the detector by the mask 20 will be modulated in correspondence with the particle structures currently imaged on the mask plane. The particle structures comprise, for example, lighter and darker regions of the particle image. During movement of the particle, the mask 20, which is fixed relative to the microsystem, transmits a larger or smaller quantity of light to the detector depending on the image brightness imaged on the segments.

The image of the particle on the mask plane is an enlarged image. The enlargement factor is selected depending on the application and is, for example, approximately 10 to 20, e.g. 15, in microsystem—microscope combinations. Characteristic dimensions of the segments 30 of the mask are in the range of approximately 100 μm (strip length).

Figure 1B:
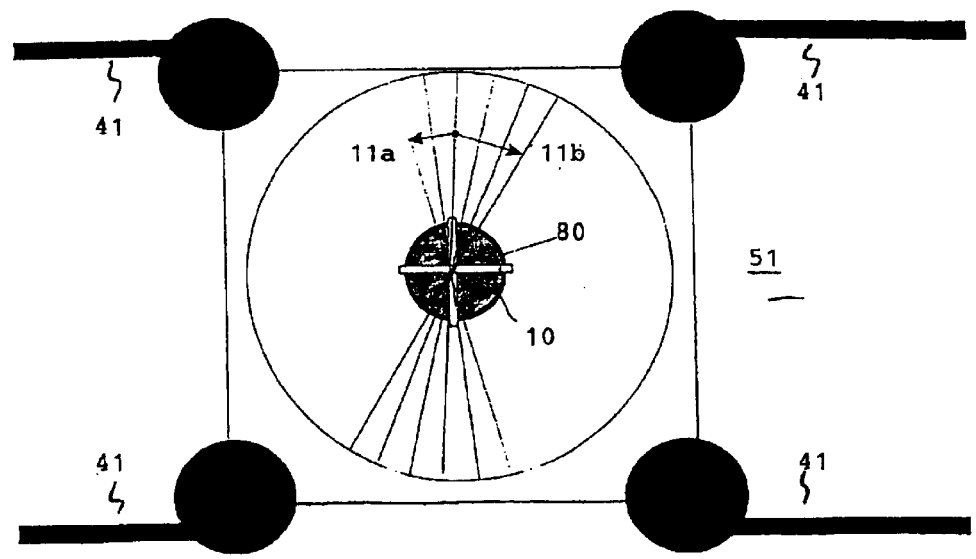

A corresponding arrangement is illustrated in top view in FIG. 1B. For dielectric single particle spectroscopy, the rotation of the particle 10 is to be detected depending on the amplitude and/or frequency of the rotational field. Information on the dielectric characteristics of the particle 10 can be determined from its angular velocity. The rotational field can rotate continuously or (as shown) have a running direction change, so that vibrations in the particle states 11a, 11b on both sides of a central position result. The section 80 covered with the cross corresponding to the mask shape is imaged via the mask. The light transmitted by the mask is modulated according to the vibrations mentioned. The vibration frequency can thus be inferred directly from the detector signal and supplied for evaluation.

Figure 2:
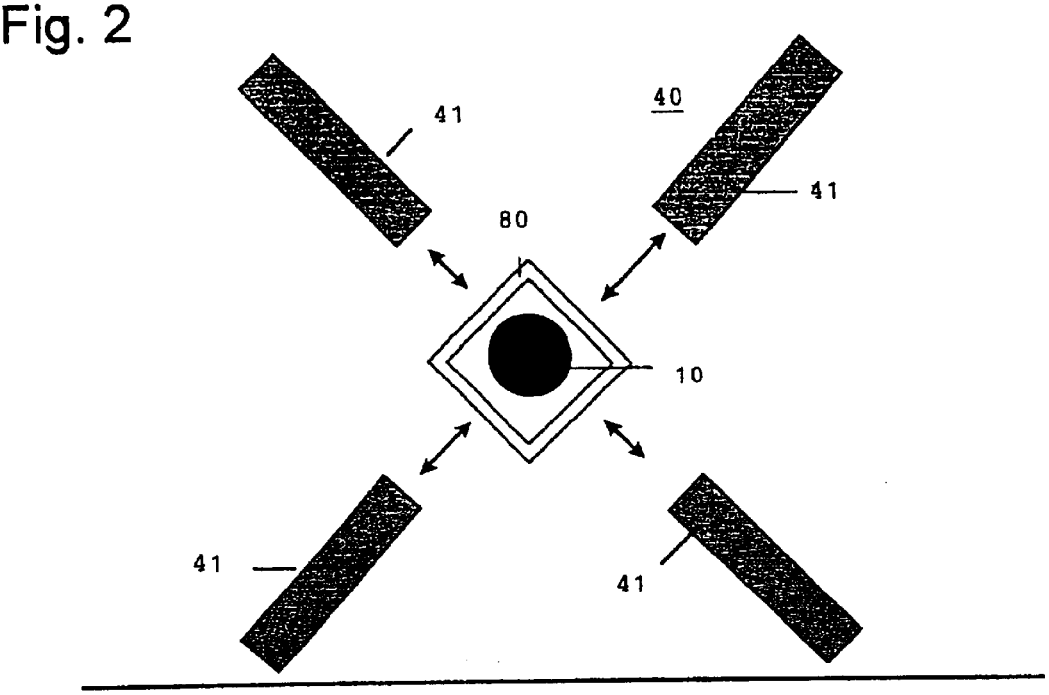
Figure 2:
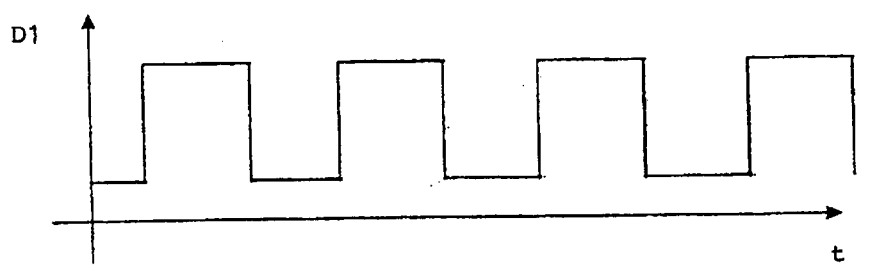
Figure 2:
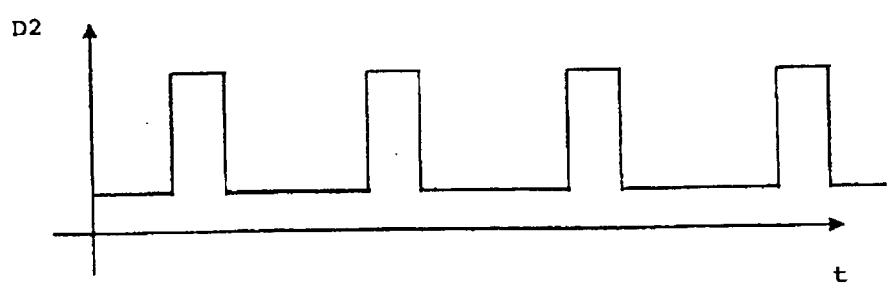

FIG. 2 illustrates an application of the invention with a modified mask design. It is emphasized that the masks are not illustrated in each of the illustrations of the FIGS. 2 to 12. In any case, each of the sections of the locational area of the particles to be detected, from which light is transmitted by the mask, are indicated. The corresponding mask segments have the same geometric shape, but are implemented larger than the sections shown due to the enlarged image introduced. The mask is structured in such a way that the light from the section 80 of the microsystem with or without the particle 10 is transmitted to the detector unit.

The design according to FIG. 2 serves for object detection for measuring dielectrophoretic characteristics of the particle 10. The particle 10 is inside a microelectrode arrangement 40, with only the electrodes 41 on the channel bottom 51 shown schematically. This electrode arrangement can in turn have four electrodes added on the channel cover to become an octopole. Other multiple electrode arrangements are also possible. At frequencies of the electrode voltages, which are selected depending on the application, the particle 10 is moved at various speeds by repulsion and/or attraction between the electrodes, depending on the external conductivity and the dielectric particle characteristics. This movement occurs periodically, for example. The particle runs, depending on its vibrational frequency, along the directions indicated with arrows (or in other directions as well) through the section 80, which corresponds exactly with the transmission geometry of the mask. The detector signal (arbitrary units) is thus modulated depending on frequency, as is indicated in the lower part of FIG. 2. The signal trace D1 corresponds to a specific frequency and a slow movement of the particle 10 between the electrodes 41. The signal trace D2 shows the same frequency, but a smaller width of the maxima of the detector signal. This corresponds to an increased movement speed of the particle 10 (and an increased displacement).

Figure 3:
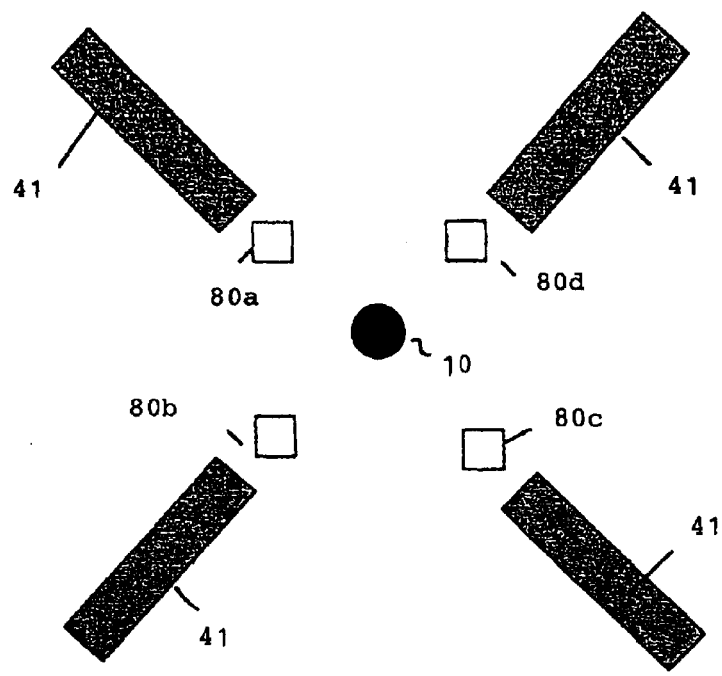
Figure 3:
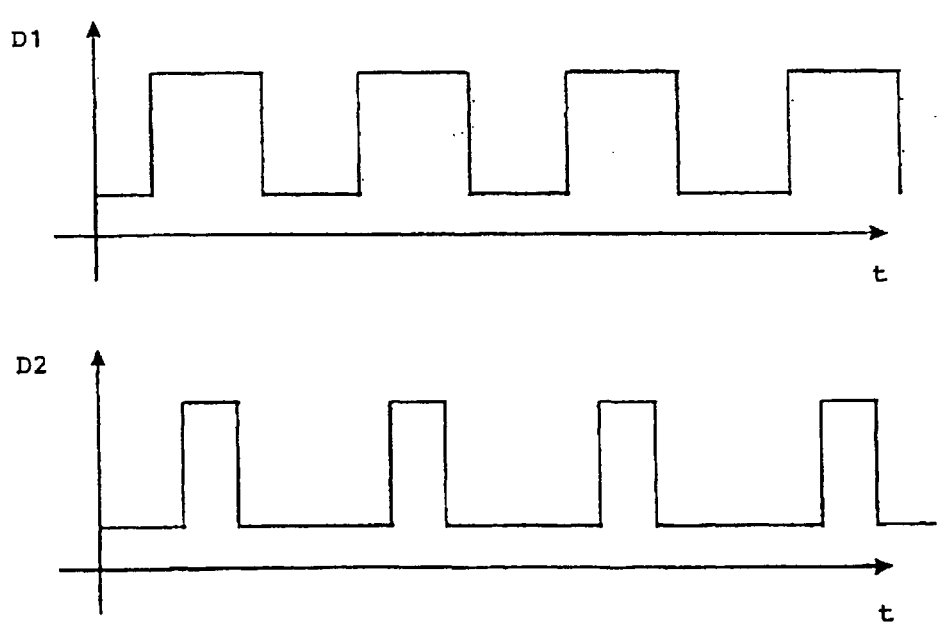

FIG. 3 illustrates a further mask design in which the mask consists of four separate quadrilateral segments positioned in such a way that the sections 80a to 80d are imaged on these segments. In this way, the period the particle 10 stays at the electrodes 41 during periodic movement can be measured (analogous to FIG. 2). The segments each serve as partial masks for object detection. The detector signal determined by the detector summarily comprises all of the quantities of light transmitted from all segments. In turn, long periods of stay (D1) can be differentiated from short periods of stay (D2) according to the lower part of FIG. 3.

Figure 4:
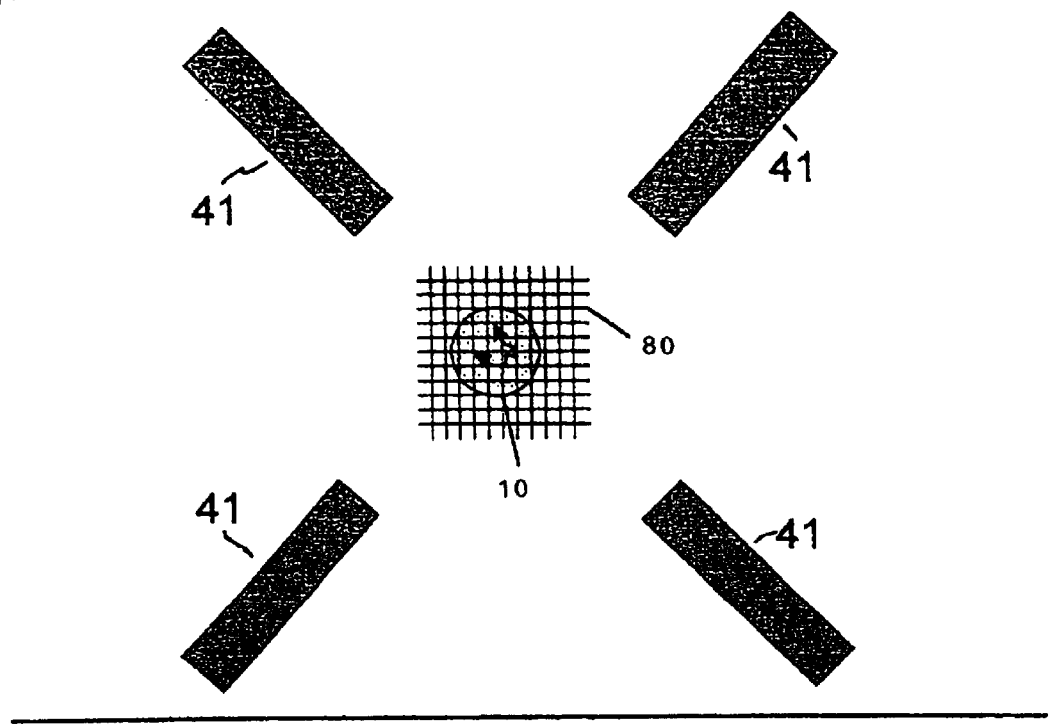
Figure 4:
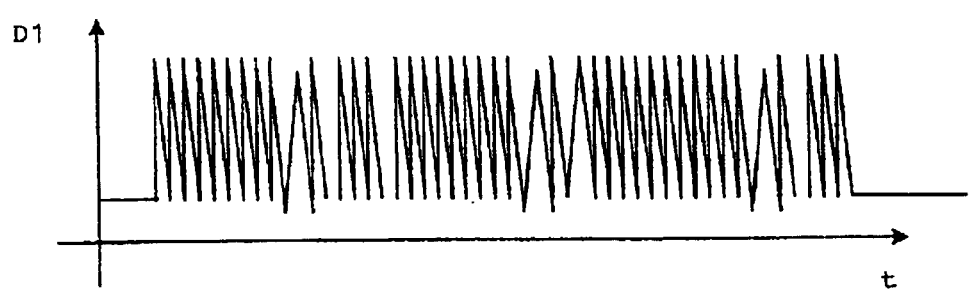
Figure 4:
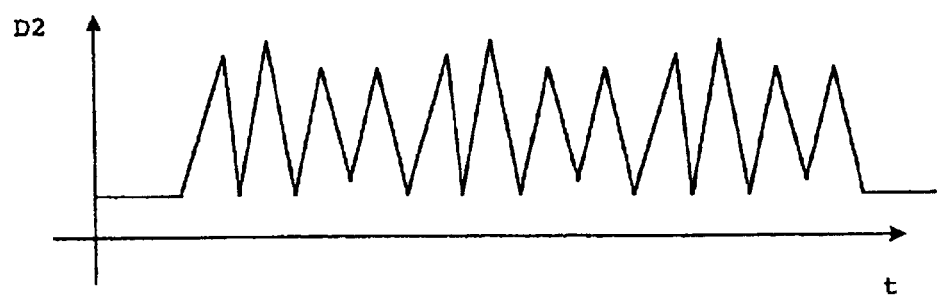

FIG. 4 illustrates object detection for the detection of the slightest thermal or hydrodynamic vibrations of a particle 10 between the electrodes 41. The mask has a gridshaped segment arrangement, so that the light from the section 80 in the microsystem is transmitted to the detector. The lower part of FIG. 4 illustrates the possibility of differentiation of stronger particle vibrations, which lead to high frequency noises D1, from smaller vibrations with a lower noise frequency (trace D2).

Figure 5:
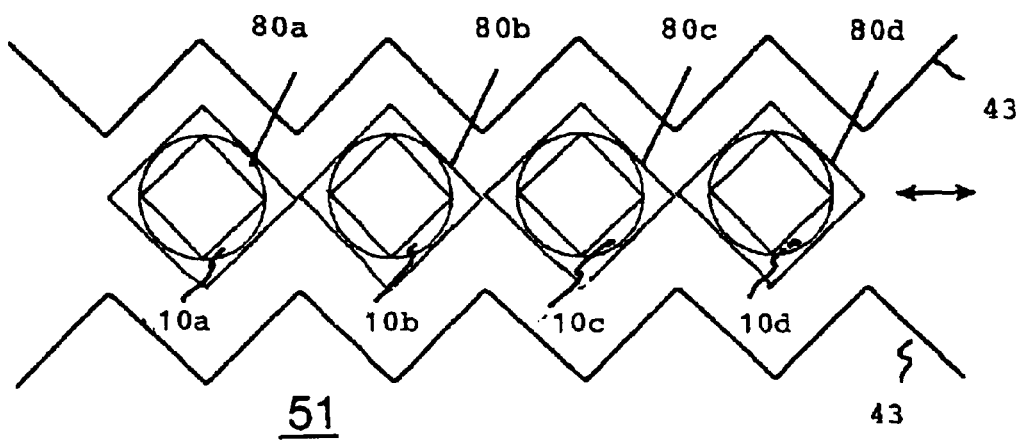
Figure 5:
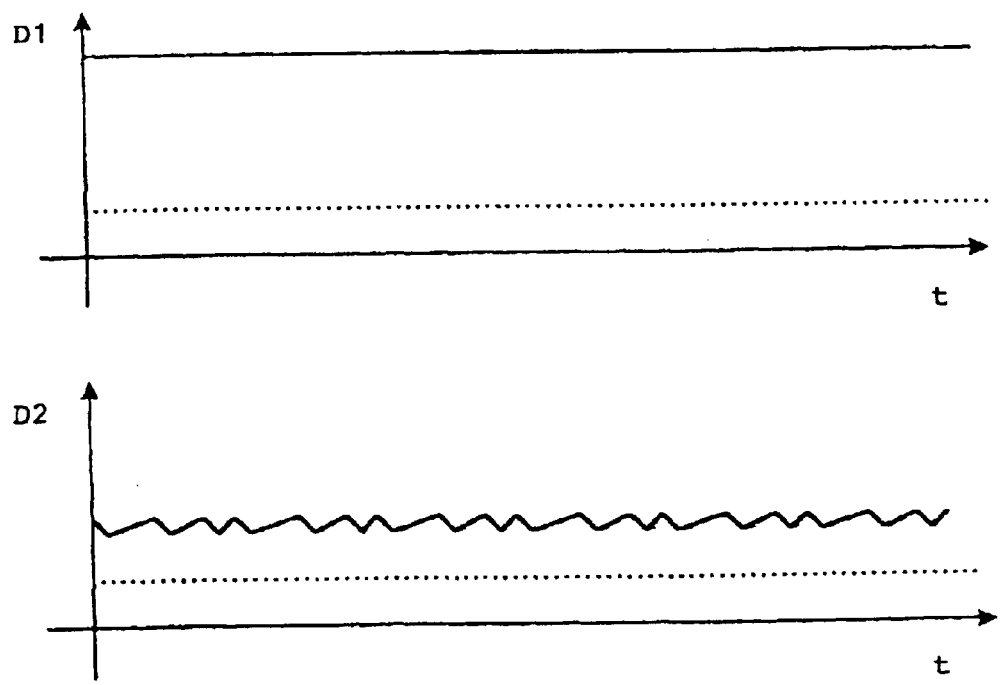

FIG. 5 illustrates an embodiment of the invention in which the presence of particles in an arrangement of electrodes in a row is investigated. The electrode arrangement 40 in this case consists of electrode bands 43 which are shaped like a triangular function. In FIG. 5, again only the electrode bands 43 on the channel bottom 51 are shown. The direction of flow in the channel is indicated by the arrow. The electrode bands 43 are driven in such a way that they form field minima at periodic intervals in which the particles 10a to 10d are to be positioned.

The mask consists of a group of segments whose number corresponds to the number of field minima of the electrode arrangement 40. Each segment forms a square frame. The segments of the mask are positioned in such a way that light from the sections 80a to 80d of the microsystem is imaged on the detector via the mask. Depending on the illumination conditions, a specific contribution to the summary detector signal results, upon the presence of a particle in a field minimum, which can assume four predetermined amplitudes in the sequence of four particles 10 illustrated. If, for example, the sequential electrode arrangement is completely filled with particles, the maximum amplitude is reached, which is illustrated in trace D1 with the solid line. In contrast, if all field minima are free of particles, the lowest amplitude results, which is shown in trace D1 with dots. As an alternative to detection of the amplitude of the detector signal, oscillations of the amplitude can also be measured. This is illustrated with the trace D2. Correspondingly, information on the stability of the particles in the sequential electrode arrangement can be inferred from this so-called variance effect.

Figure 6:
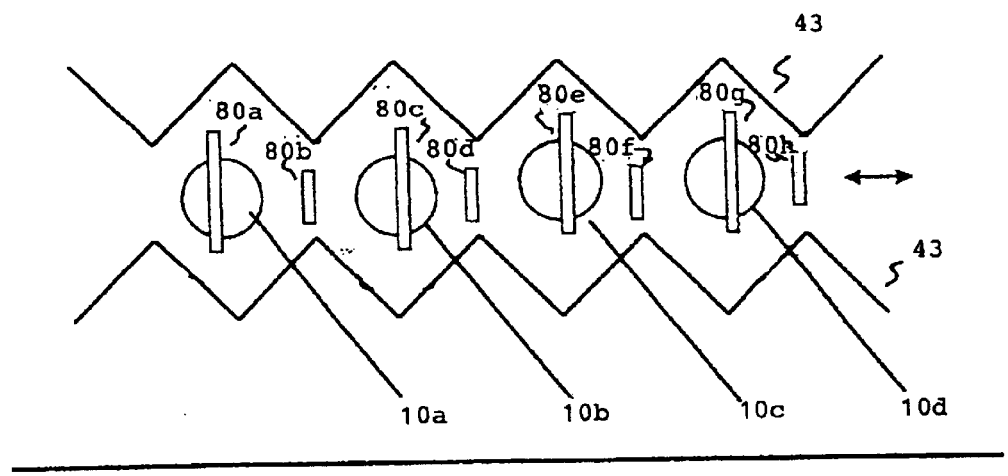
Figure 6:
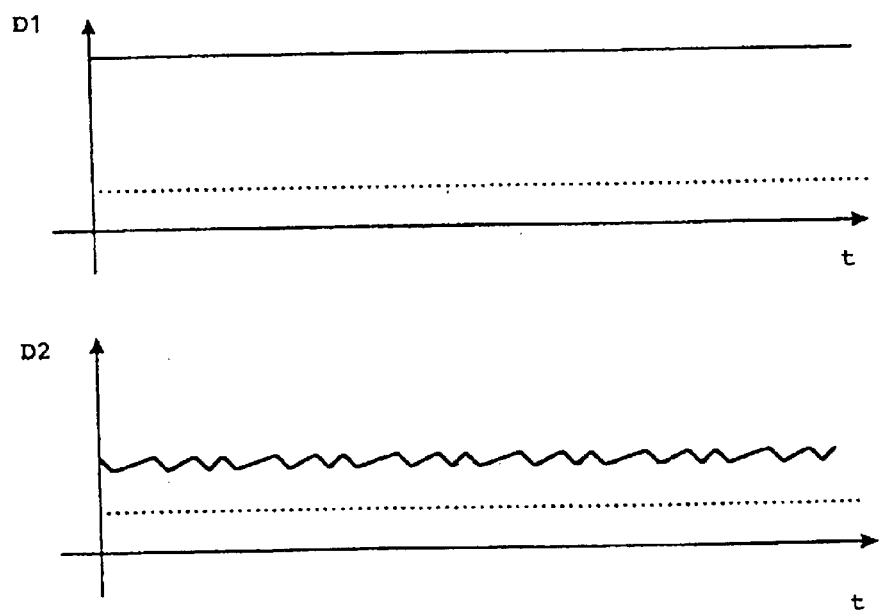

A modified mask design for examining the particle sequence is illustrated in FIG. 6. The mask consists of strip-shaped segments at intervals from one another which image the sections 80a to 80h of the microsystem on the detector. The segment strips have alternating varying lengths and are positioned in such a way that the longer segment strips detect the sections 80a, 80c, 80e, and 80g corresponding to the field minima between the electrode bands 43 and the shorter segment strips detect the sections 80b, 80d, 80f, and 80h of the microsystem. The detector signal has, in turn, a trace which essentially corresponds to the illustration in the lower part of FIG. 5, with, however, additional amplitude steps corresponding to the particle detection occurring at the locations between the field minima.

Figure 7:
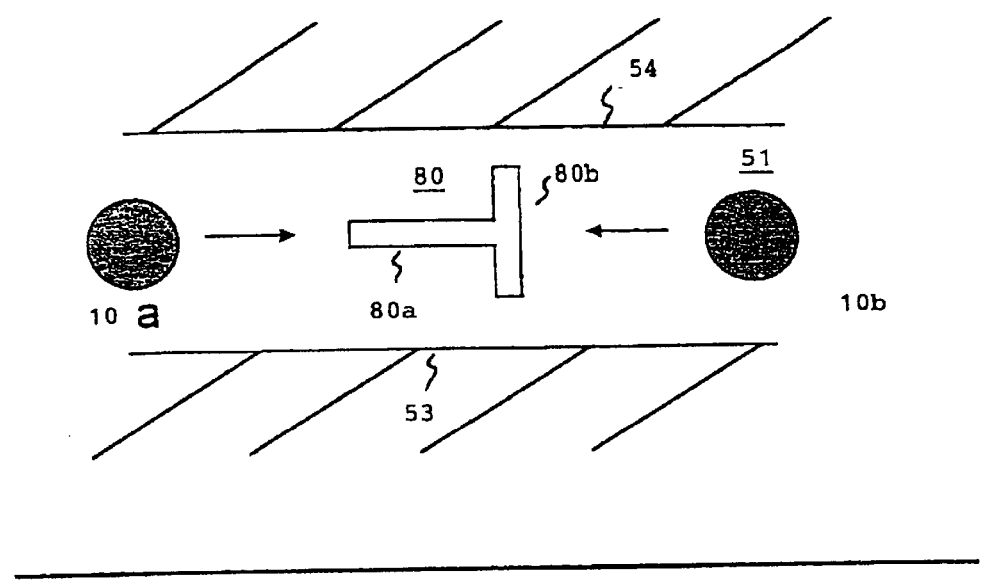
Figure 7:
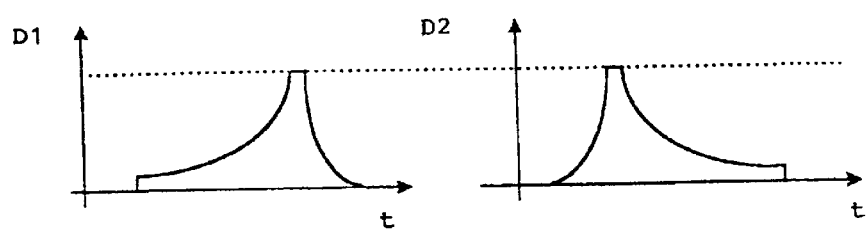
Figure 8:
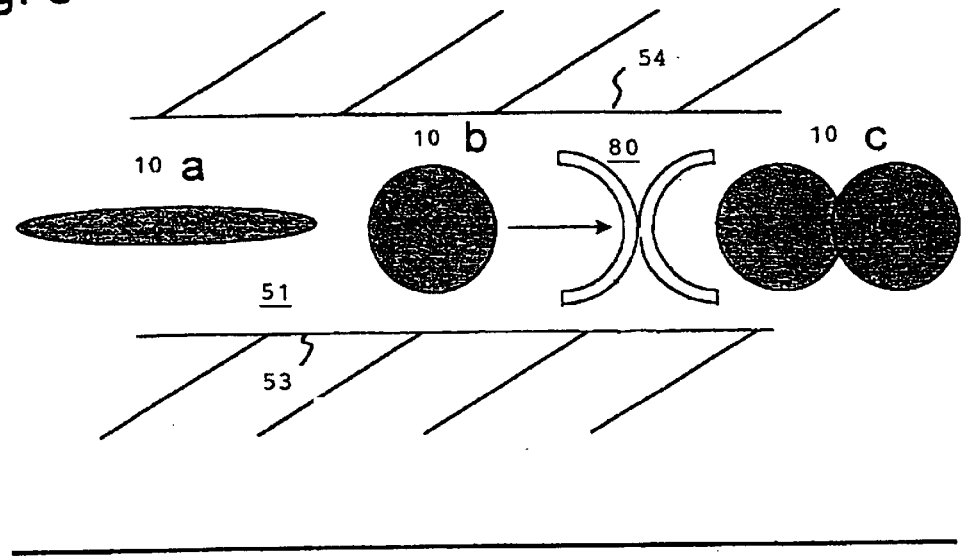
Figure 8:
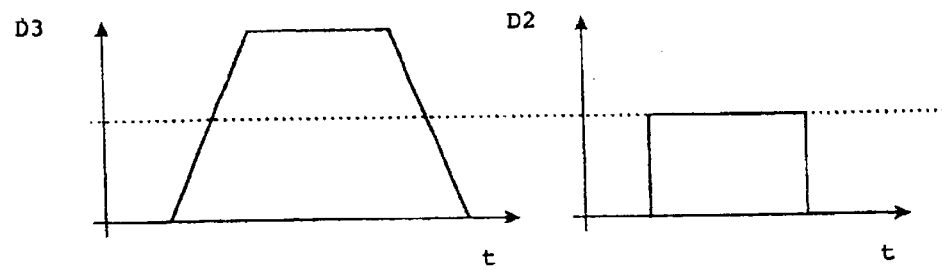
Figure 8:
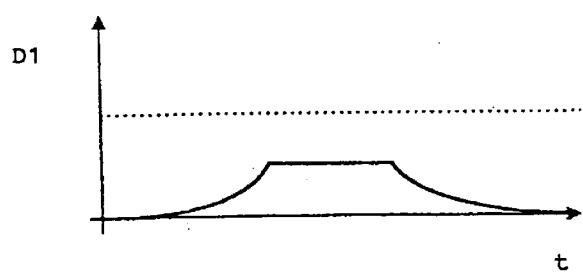

FIG. 7 illustrates the principle of the detection of the movement direction according to the invention. The upper part of FIG. 7 is a schematic top view of a channel in which the channel side walls 53, 54 adjoining the channel bottom 51 are also illustrated. The mask has a T-shaped transmission geometry and is formed by two straight strip-shaped segments, with one longer segment aligned in the lengthwise channel direction (corresponding to the direction of the arrows) and a shorter segment strip running perpendicular to this at the end of the longer segment strip. The image on the mask leads to transmission of the light from the T-shaped section 80 of the microsystem to the detector.

The detector signal then has one of the traces illustrated in the lower part of FIG. 7, depending on the movement direction. The particle 10a, which moves from left to right, contributes first at the lengthwise strip 80a and then at the transverse strip 80b to the detector signal, which, corresponding to the trace D1, first slowly increases as the particle passes through and then quickly drops after the particle 10a passes the transverse strip 80b. For the particle 10b, which moves from right to left, the reverse relationships result. The detector signal first increases quickly and then drops slowly, corresponding to the trace D2. The detector signal thus has a characteristic time characteristic which provides information on the movement direction of the particle in the channel.

A mask according to the invention can also be designed in such a way that differences in shape of particles in the microsystem can be detected. This is illustrated in FIG. 8, which again shows a top view of the channel with the channel bottom 51 and the channel side walls 53, 54. Particles 10a, 10b, and 10c, which have various geometries, move in the channel.

The mask consists of two strip-shaped segments which are each curved into a semicircle and which touch at their apexes. In this way, the mask allows the transmission of the light coming out of the section 80 of the microsystem to the detector. Depending on the time characteristic of the detector signal, the respective particles passing by the section 80 can be distinguished. This is illustrated in the lower part of FIG. 8.

The oblong particle 10a generates a signal trace D1 because the detector signal is modulated for a relatively long time, but only has a relatively low amplitude due to the small transverse extension of the particle 10a. For a round particle 10b, to whose shape the semicircular curvature of the mask segments is tailored, the trace D2 results. The entrance of the particle 10b into the section 80 causes a rapid signal increase. A corresponding situation applies for the case when the particle 10b leaves the section 80. Finally, the particle 10c (pair) leads to the signal trace D3, which extends over a larger time range than particle 10b due to the greater lengthwise extension and reaches a higher amplitude than particle 10a due to the larger transverse extension.

Figure 9:
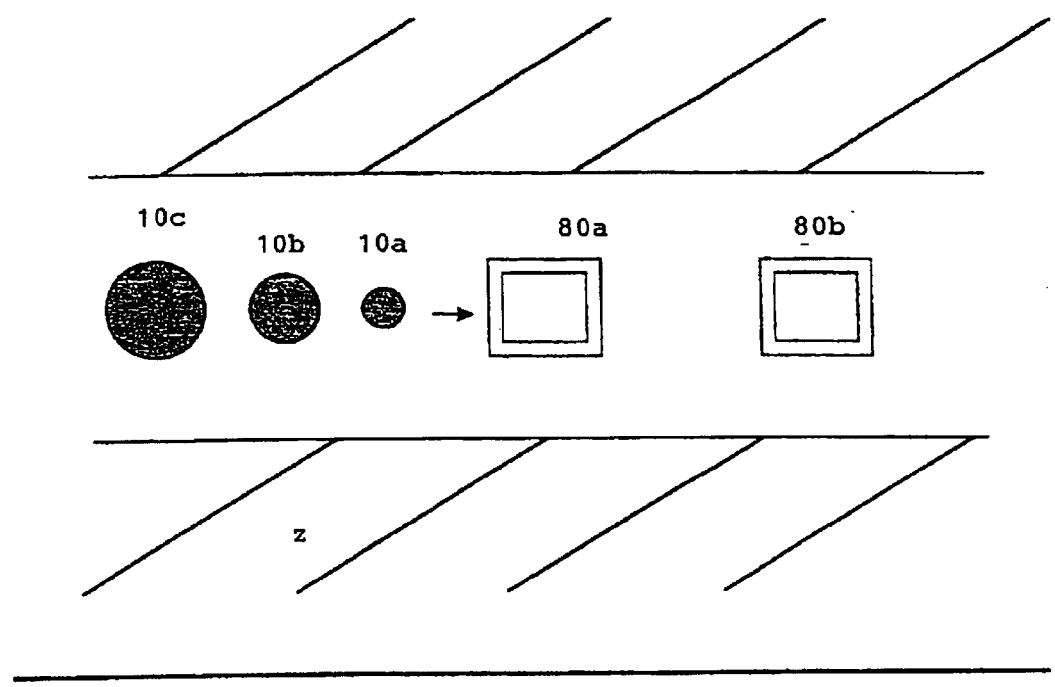
Figure 9:
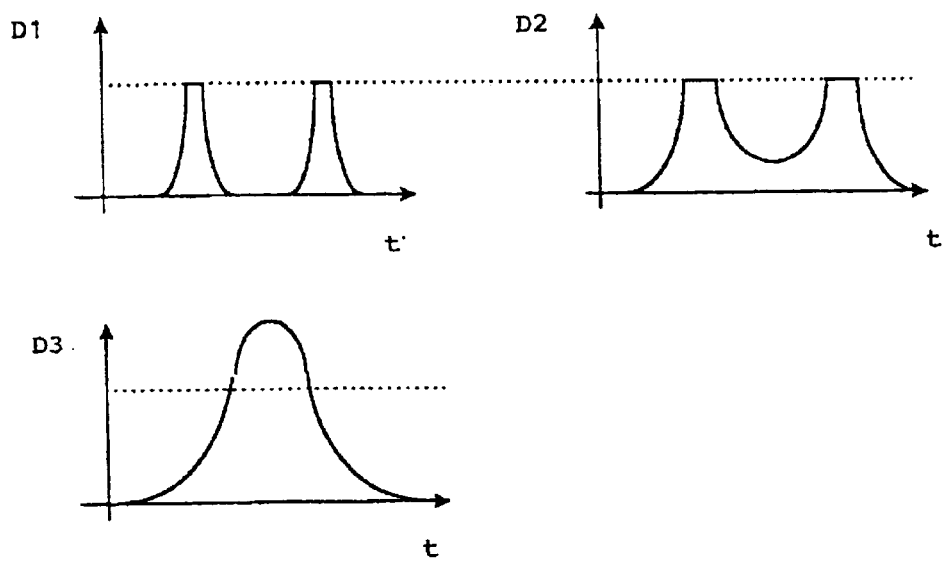
Figure 10:
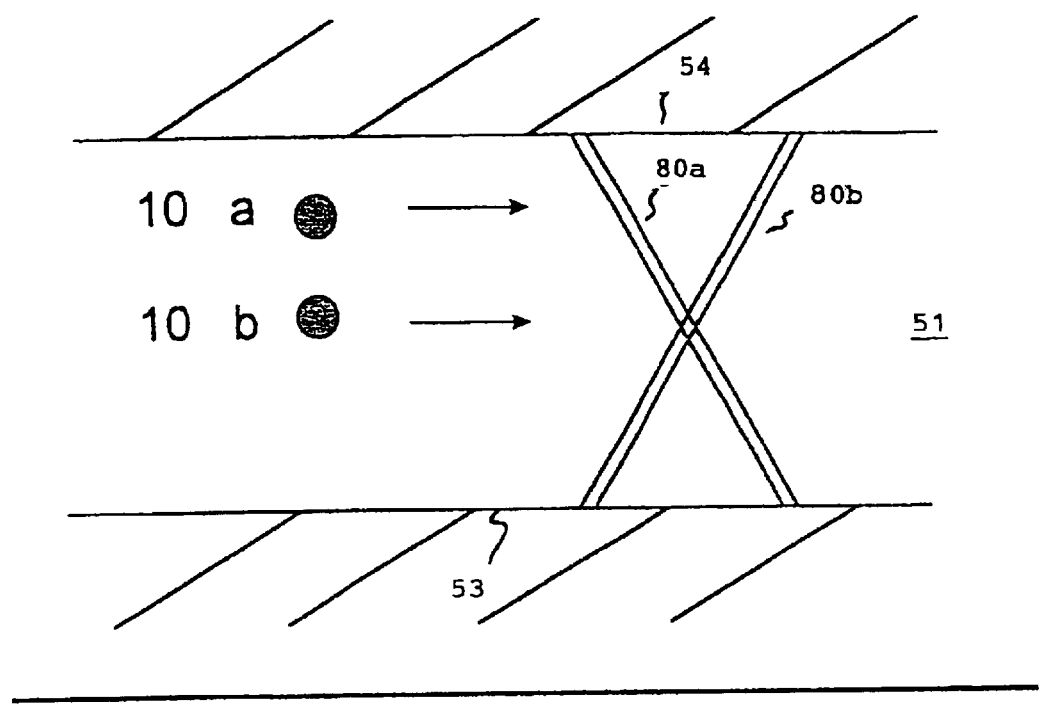
Figure 10:
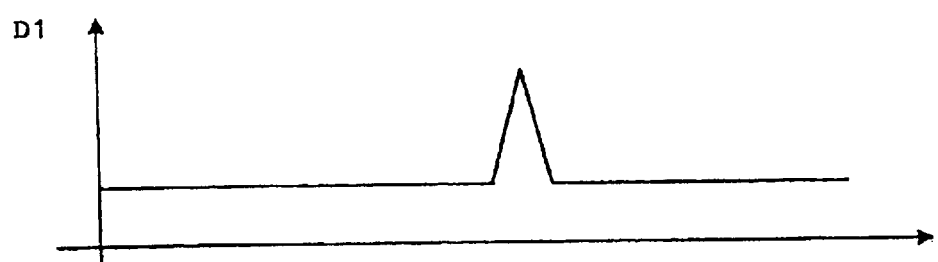
Figure 10:

The mask shape described above with reference to FIG. 2 can also be used for particle counting, as is illustrated in FIG. 9. The mask contains two segments which are set up for transmission of light from the sections 80a, 80b and which each have the shape of a square frame. The sections 80a, 80b are positioned in the lengthwise channel direction at a predetermined interval. The selection of the interval and the size of the sections 80a, 80b (and/or the corresponding mask segments) is selected depending on the particle sizes occurring and the flow speed in the channel. The particle counting can even be performed size-selectively.

Thus, the smallest particle 10a produces the signal trace D1 with two separate maxima corresponding to the passage of the particle 10a at each of the sections 80a, 80b. For the medium particle 10b, the signal trace D2 results, in which the maxima run into one another. For a sufficiently large particle 10c with a characteristic size which is comparable with the interval of the sections 80a, 80b the signal trace D3 with one single maximum results. The signal traces D1 and D2 can additionally be used to determine the particle speed from the interval of the maxima.

FIG. 10 again shows a top view of the channel with the channel floor 51 and the channel side walls 53, 54. In the channel, particles 10a, 10b move with the flowing suspension fluid according to the direction of the arrow. The object detection according to the invention is designed here in such a way that it is determined whether a particle moves in the center of the channel or more at the edge of the microchannel. For this purpose, the mask has two segments made of straight, crossing strips which are positioned in such a way that the light from the sections 80a, 80b of the microsystem is transmitted to the detector. The sections 80a, 80b each extend as straight strips over the entire width of the channel and are curved relative to the transverse channel direction, so that an X-shape with the strips intersecting in the center of the channel results.

Detection through a mask which transmits the light from sections 80a, 80b selected in this way results in a signal trace D1 with one single maximum if the particle 10b moves in the center of the channel or a signal trace D2 if the particle 10a moves at the edge of the channel, so that each section 80a, 80b is crossed two times.

Figure 11:
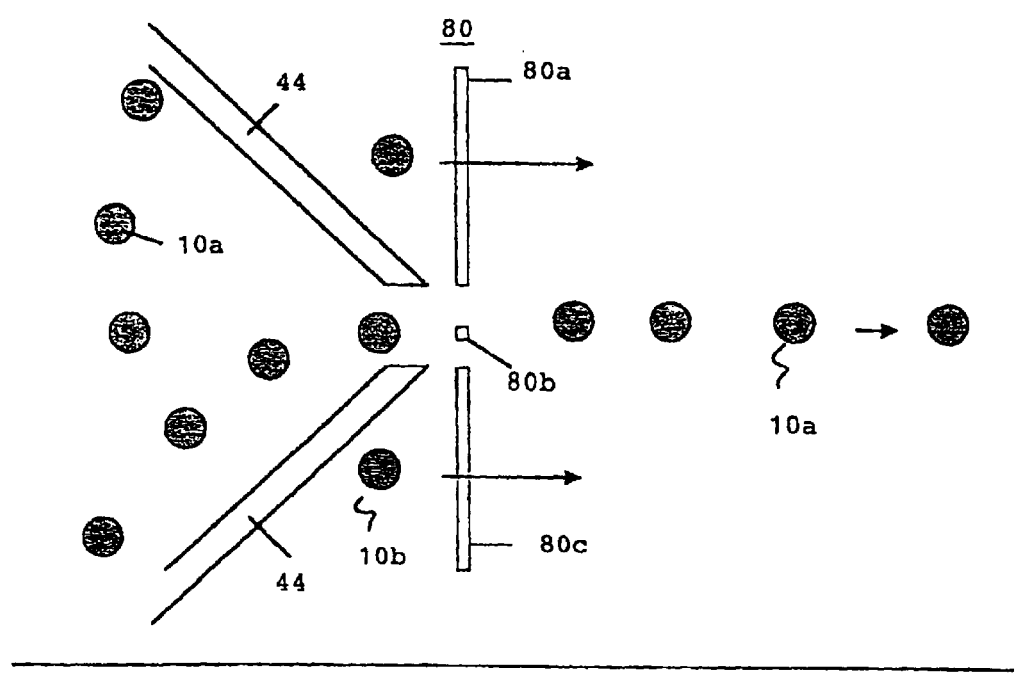
Figure 11:
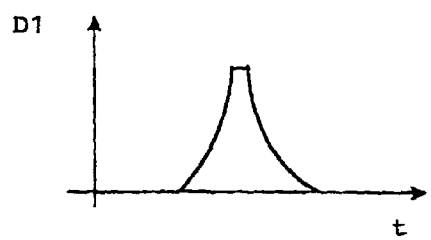
Figure 11:
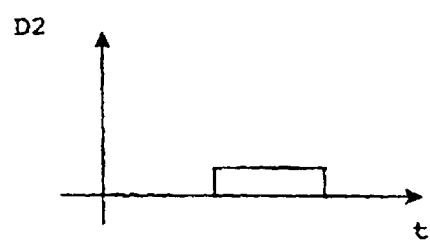

A similar monitoring function is illustrated in FIG. 11, which depicts a top view of a channel with focusing electrodes 44 on the channel bottom 51. The focusing electrodes 44 form field barriers, which the particles 10a cannot penetrate, when high frequency voltages are applied to them, so that, in combination with the force of the flow, a particle movement toward the center of the channel occurs. If one of the focusing electrodes 44 fails, particles 10b can pass by the electrodes except at the center.

In order to detect this type of malfunction of the focusing electrodes 44, the mask is designed in such a way that particles at the channel edge can again be distinguished from particles in the center of the channel. For this purpose, the mask has three segments, comprising two straight strip-shaped segments and one dot-shaped segment, which are positioned in a straight row transverse to the lengthwise channel direction. The segments are set up for the purpose of transmitting the light from the sections 80a, 80b, and 80c of the microsystem to the detector. After the passage of each of the particles 10a through the center or the particles 10b through the edges of the channel, the signal traces shown in the lower part of FIG. 11 result. The signal trace D1 shows a high amplitude, i.e. a strong modulation of the detector signal. This indicates the particle 10b has passed through the sections 80a or 80c and therefore one or both of the focusing electrodes 44 is switched off or defective. In contrast, the signal trace D2 shows a small modulation corresponding to particle passage through the center of the channel. The signal corresponding to the signal trace D2 can in turn be used as the count signal for counting the particles 10b which have passed the focusing arrangement.

Figure 12:
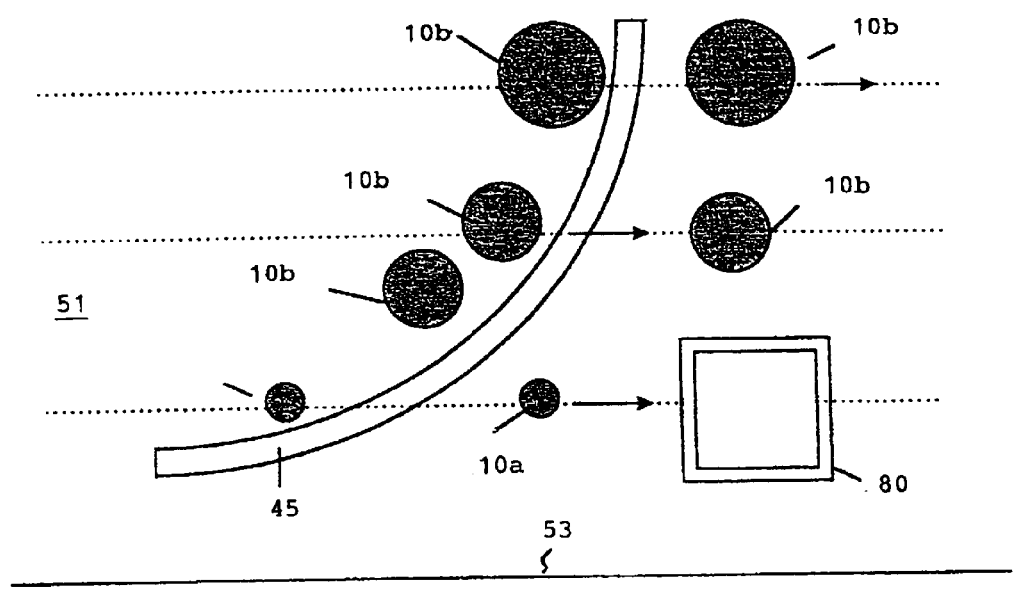
Figure 12:
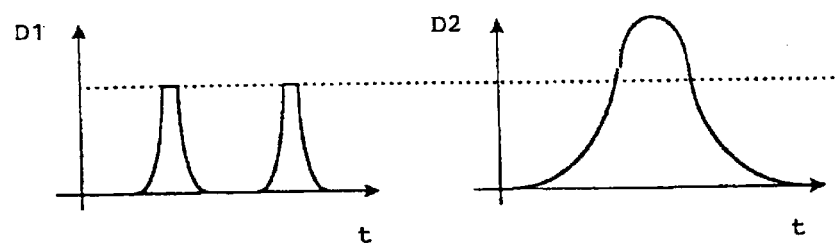

A mask such as that described with reference to FIG. 2 can also be used for checking the function of a deflection electrode 45. This application of the invention is illustrated in FIG. 12. The deflection electrode 45 is a micro-electrode on the channel bottom 51 in the shape of a curved electrode strip. The deflection electrode 45, in combination with a corresponding deflection electrode (not shown) on the channel cover, forms a curved field barrier, when high frequency voltages are applied to it, which the flowing particles 10a and/or 10b can pass at various distances from the channel side walls 53, depending on their dielectric characteristics. If the deflection electrode 45 is switched on, the smallest particles 10a, in which the smallest polarization forces are induced, can pass the field barrier even at the edge of the channel, while the larger particles 10b run further toward the center of the channel until the force of the flow is sufficiently large that passage of the field barriers is effected. If the deflection electrode 45 is switched off, both large and small particles can flow further at the channel edge.

The mask has a square, frame-shaped segment which is set up for the purpose of transmitting the light coming out of the section 80 of the microsystem to the detector. If only small particles 10a pass by the section 80, then the signal trace D1 with two separate maxima occurs, corresponding to the passage of the small particles 10a at the two frame sides in the direction of flow. If the deflection electrode 45 is switched off or defective, then larger particles are also detected via the mask, so that the signal trace D2 occurs, with one single, widened maximum.

The above exemplary embodiments described with reference to FIGS. 1 to 12 relate to particle detection in microsystems, known per se, with channel structures made of materials which are inert relative to the particles. The FIGS. 13 to 15 described below show a particularly advantageous application of the invention in modified Microsystems in which the interaction of the particles with the channel walls is not avoided, but encouraged in predetermined ways. This modification is illustrated in FIGS. 13A and 13B in analogy to the illustration according to FIG. 1.

Figure 13A:
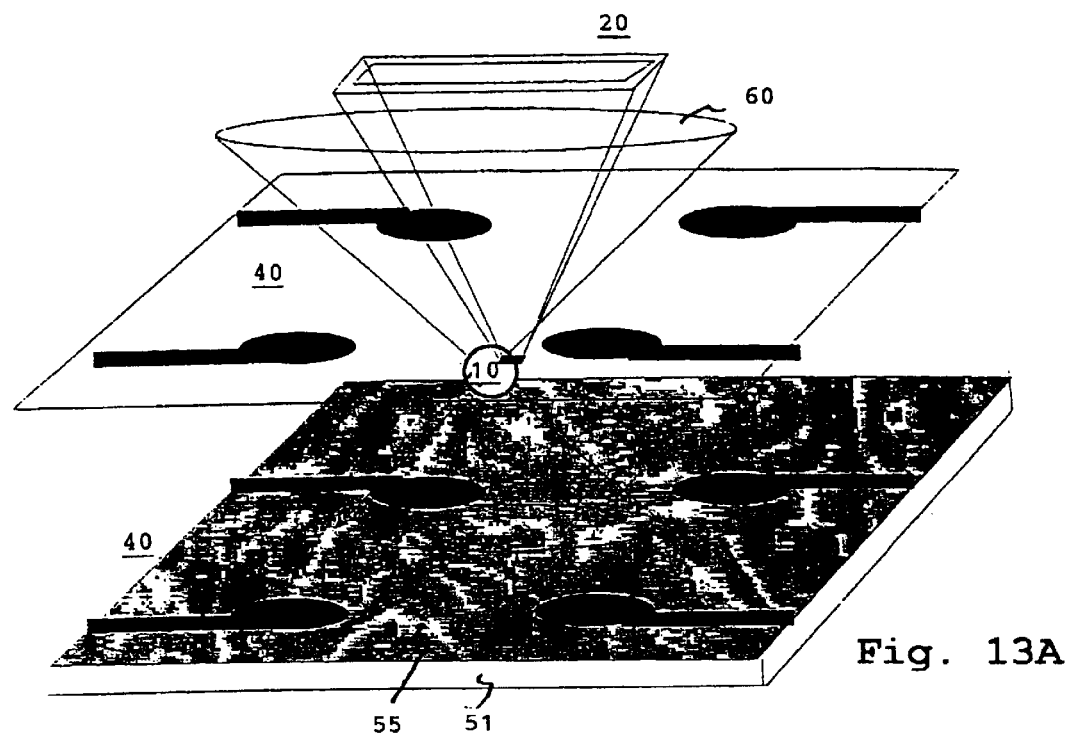
Figure 13B:
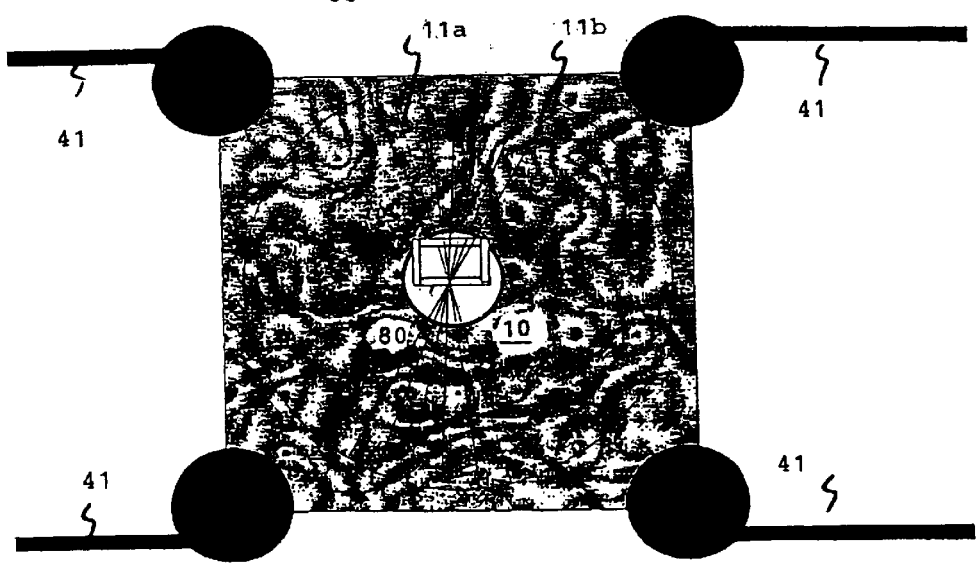

FIG. 13A shows a schematic perspective view of a section of a fluidic microsystem as in FIG. 1. However, in this case the channel bottom 51 forms a substrate for a modification layer 55. The modification layer 55 consists, for example, of a monolayer of biological cells. Again, the movement of the particle 10 is to be detected with object detection according to the invention, as described above, which occurs here through a frame-shaped mask 20. The particle 10 is a test object, which can be a biological cell or an artificial particle with specific or nonspecific binding sites (molecules). The movement of the particle 10 is influenced by the interaction with the modification layer 55, i.e. by the occurrences of adhesion which arise.

To determine the adhesion characteristics of the particle 10 relative to the modification layer 55, i.e. to determine binding forces, binding constants, and/or the dynamics of cell adhesion, the particle is pressed with the aid of the trapping laser 60 onto the surface of the modification layer 55 while the rotating field of the electrode arrangement 40 induces oscillating rotations to the left or right. The oscillatory particle vibrations in the states 11a, 11b are detected via the mask 20 as described above. Through comparison with the movement characteristics without adhesion, information on the binding forces and similar characteristics can be obtained. Other mask shapes which are different from the frame mask 20 illustrated can also be used. FIG. 13B shows the corresponding situation in a top view.

Figure 14:
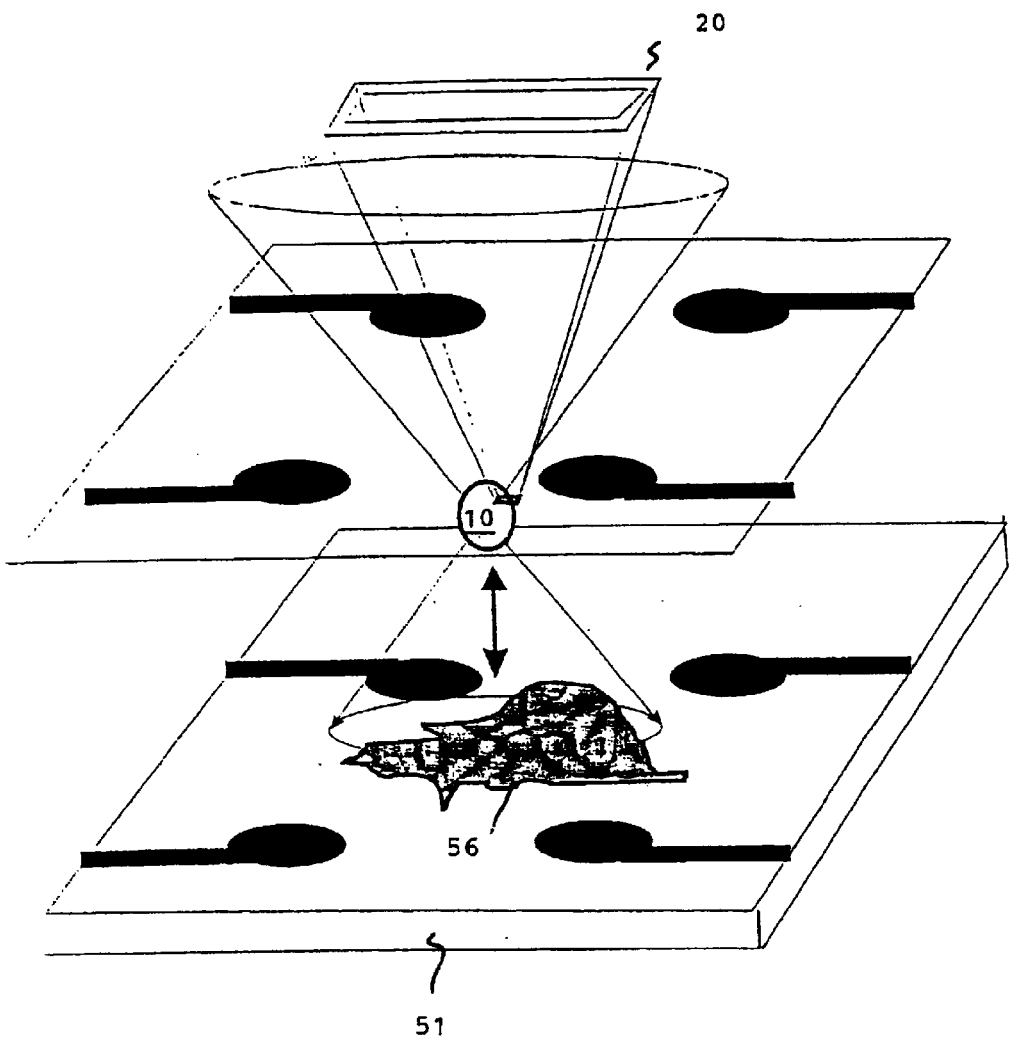

The modification can also be formed by one single particle on the channel floor 51. This situation is illustrated in FIG. 14. A biological cell 56 is on the channel floor 51. The detection of the particle movement of the particle 10 according to the invention again occurs depending on the interaction with the cell 56. For sufficiently small particles (diameter smaller than 5 μm) the surfaces of the cells 56 can also be measured with localized resolution. There is also the possibility of connecting the locally resolved partial measurement of the interactions of the cell 56 with the particle 10 with a chemical stimulation of the attached cell 56.

Figure 15:
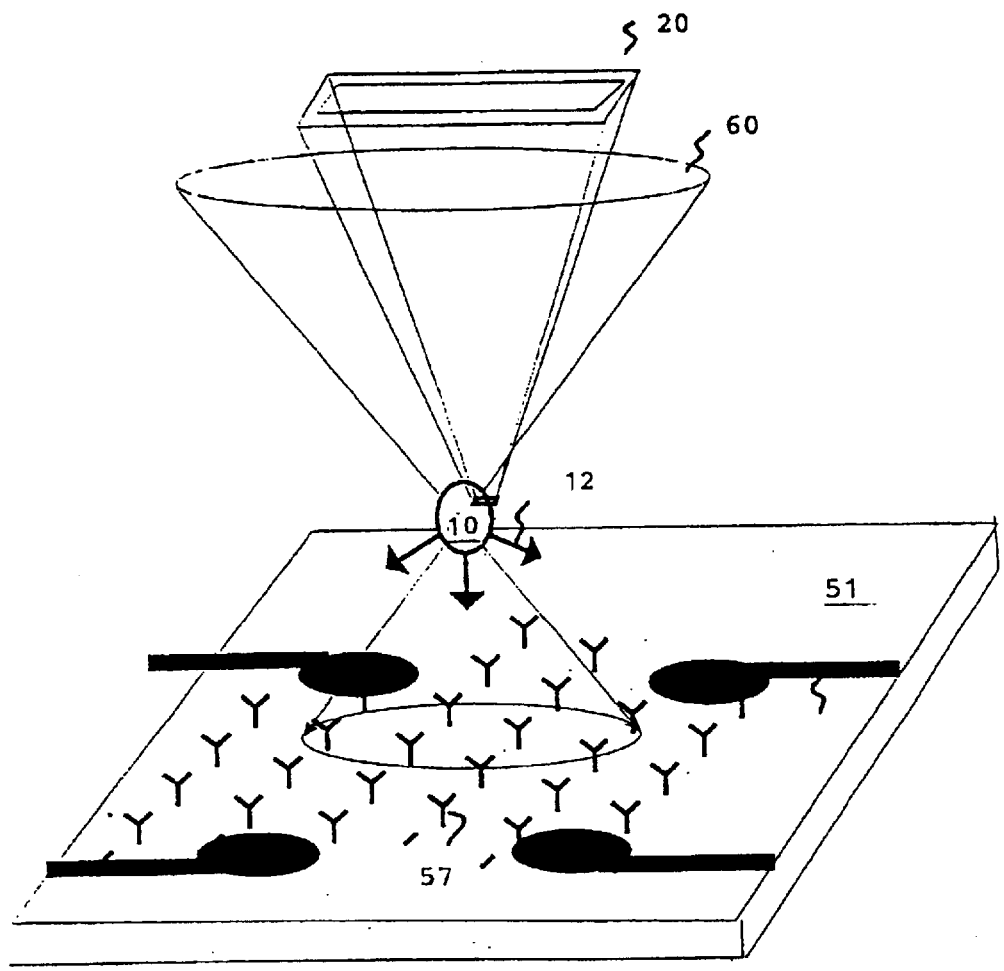

FIG. 15 shows a further modification of object detection for the determination of interactions of a particle with a modification layer on the channel floor 51. The modification layer consists of multiple molecular receptors 57. The particle 10 has ligands 12. The particle rotates as described above with reference to FIG. 1. It can be determined from the particle detection whether the ligand 12 undergoes binding with the receptors 57. The particle 10 can itself be a biological cell or a cell component and can carry a receptor on its surface depending on natural conditions.

Figure 16:
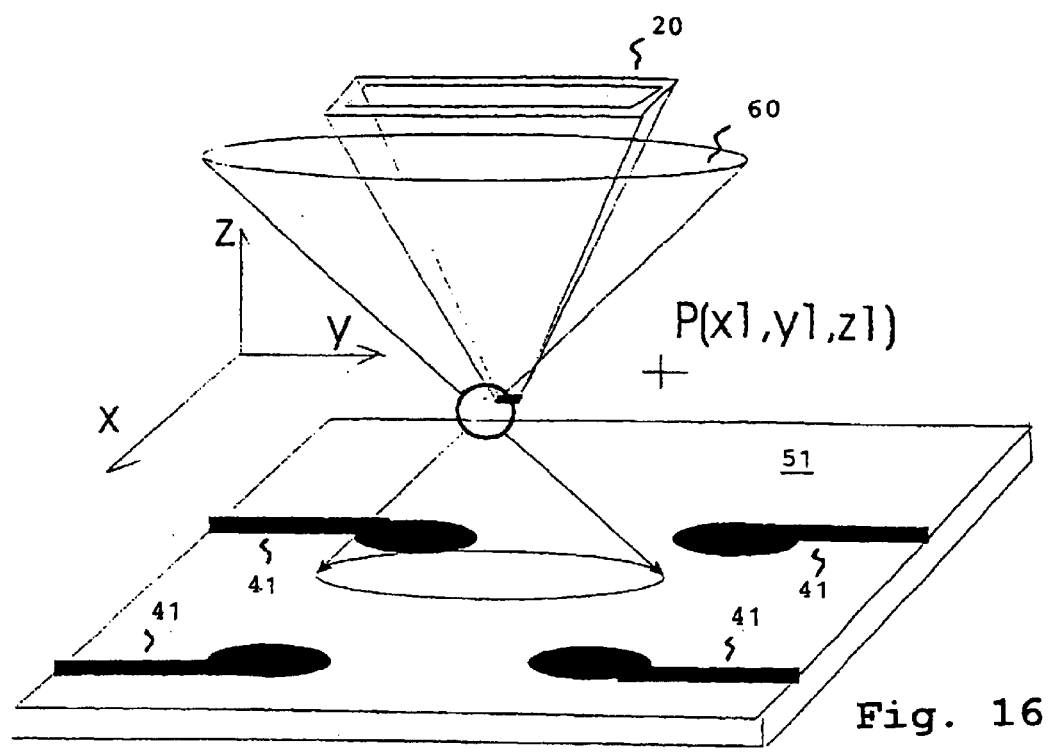
Figure 17:
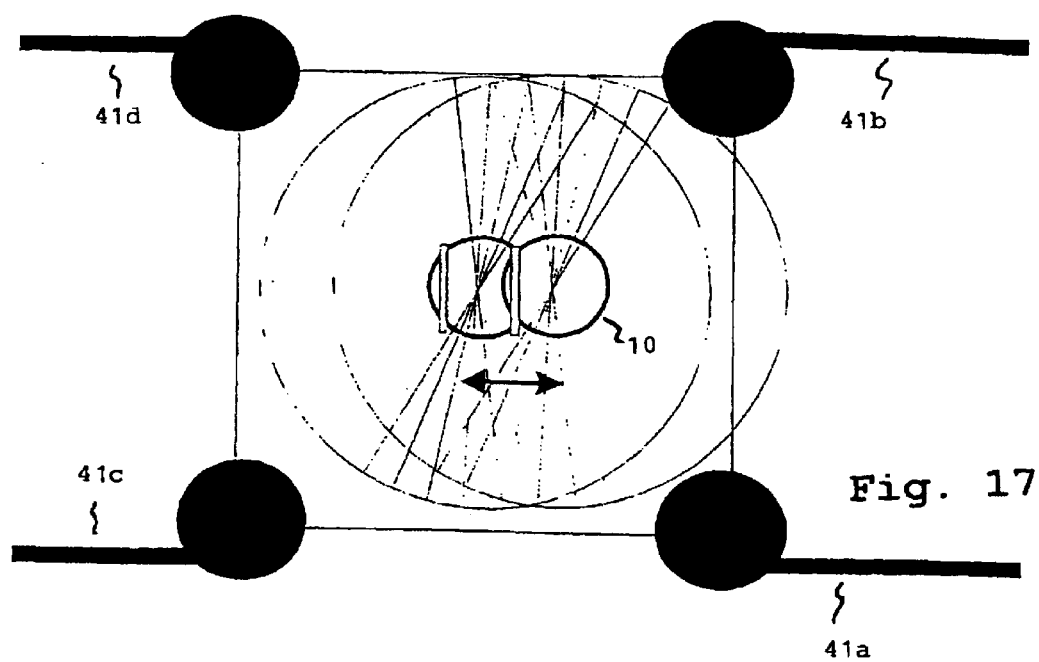

A further application of the invention for measurement of forces in a microsystem is illustrated in FIGS. 16 and 17. Analogously to FIG. 1, FIG. 16 shows a section of a microsystem with the channel bottom 51 and the lower microelectrodes 41. The particle 10 is guided to a predetermined position P having the coordinates (x1, y1, z1) with the trapping laser 60 and there is subjected to the rotating fields of the electrode arrangement. The imaging unit with the mask 20 is appropriately adjusted to detect the object movement. The angular velocity of the particle 10 measured at point P has a direct relationship to the field strength at this location (the angular velocity is proportional to the square of the field strength). In this way, the electromagnetic field in the microsystem in the x, y, and z directions can be measured with the object detection according to the invention using a small test particle, in that the test particle 10 is scan-like moved to various spatial positions between the microelectrodes and subjected to a rotation measurement.

For this measurement, a mask design can also be provided with which the particle movements in the entire region between the microelectrodes can be detected. In this case, the mask 20 does not have to be displaced upon adjustment to a new point P.

A further mask design with two strip-shaped segments (detection slits) is used according to FIG. 17 for determination of particle movements in the direction of the arrow. The movement of the particle 10 in the x direction is performed with the trapping laser (not shown) or through shifting the amplitudes of the high frequency voltages on the electrodes 41a, 41b and/or 41c, 41d. Information on dielectric particle characteristics, the field strength in the focus of the trapping laser, and the electromagnetic field strength can be derived from the deflection of the particle.

Analogously to the techniques described in FIGS. 15 to 17, a measurement of the field strength in the trapping laser 60 through measurement of the rotational speed of a test particle depending on the distance from the focus of the trapping laser can also be used.

Figure 18:
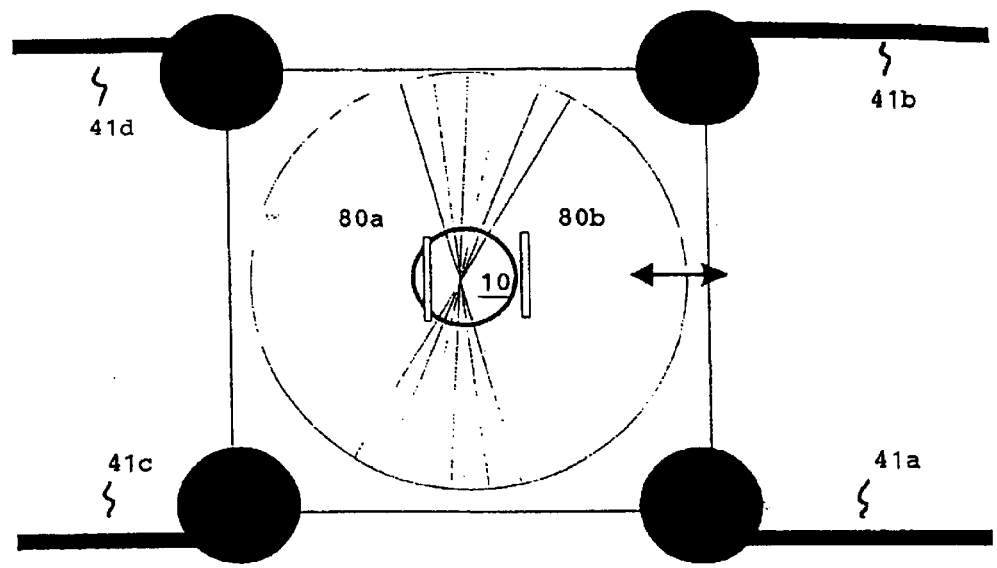
Figure 18:
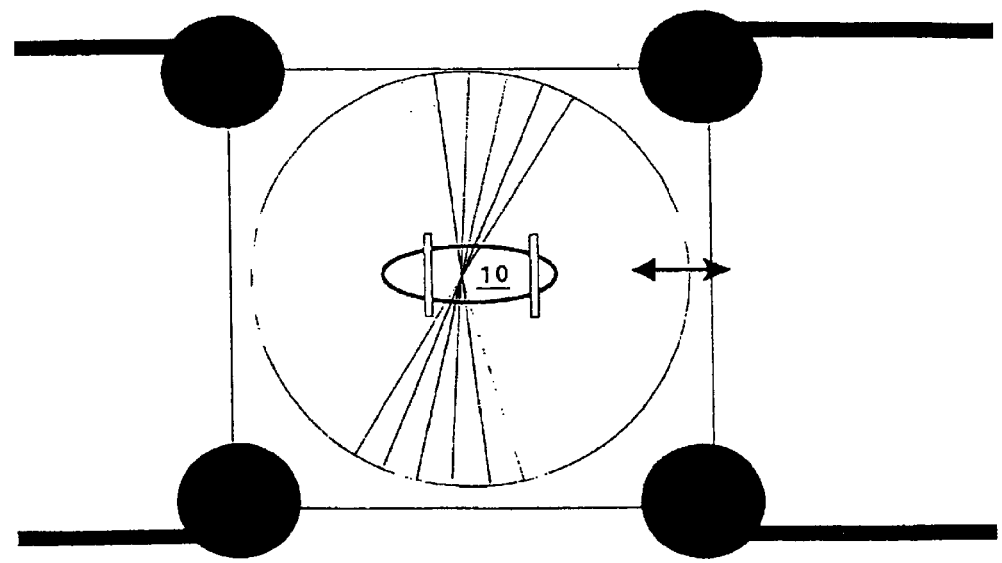

Object detection according to the invention is also usable for detection of particle deformations. This is illustrated in FIG. 18. The particle 10 is deformed by adjustment of an inhomogeneous high frequency electric field on the electrodes 41a, 41b and/or 41c, 41d while it is held in free suspension with the trapping laser. The deformation can, for example, lead from a round particle shape (upper part of FIG. 18) to an elliptical particle shape (lower part of FIG. 18). With a slit mask, having two strip-shaped segments which are set up to transmit light from the sections 80a, 80b of the microsystem to the detector, the asymmetry of the particle 10 can be detected. Mechanical characteristics of the particle (e.g. biological cell) can be estimated from the deformation, which is derived from the detector signal. Depending on the application, other mask shapes which are adjusted to the respective asymmetries can also be used for examination of the deformation.

Figure 19:
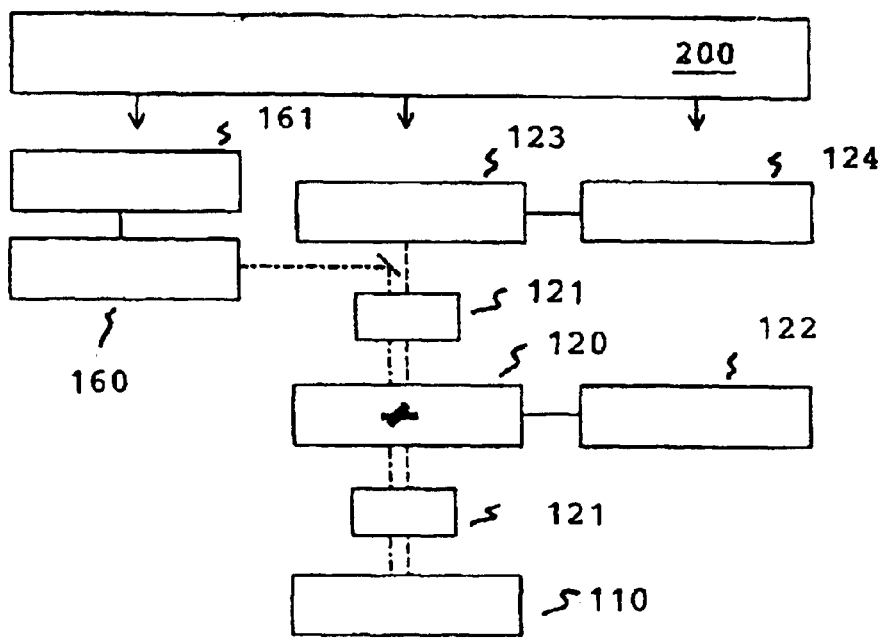

FIG. 19 is an overview illustration of a device according to the invention for object detection with implementation of the invention on a fluidic microsystem. The fluidic microsystem 110, which contains a suspension with at least one particle to be examined, is driven via a control device 111. If the microsystem contains microelectrodes for dielectric particle manipulation, then the control device 111 particularly contains a generator for driving the electrodes.

The region of interest of the microsystem 110 is imaged via optical elements 121 enlarged on the structured mask 120, which can be adjusted in relation to the microsystem with an adjustment unit 122. In an integrated manner, the light passing through the structured mask 120 is imaged on the detector 123 (e.g. photodiode) by further optical elements 121, which possibly include a stop filter for the light of the trapping laser 160. The detector 123 is connected with an evaluation unit 124 which particularly contains a computing unit for evaluating the signal traces and a display unit for visual depiction of the object characteristics detected. The evaluation of the signal traces is performed in a way known per se, particularly in regard to the temporal position of the maxima, the amplitudes of the signals, and their phase positions.

FIG. 19 further shows the trapping laser 160, which is controlled via a separate laser tweezers control 161. The reference sign 200 indicates an overall control unit for synchronous operation, depending on the application, of the laser control 161, the control unit 111, and the adjustment unit 122.

The imaging unit with the optical elements and the structured mask 120 is preferably integrated in a microscope whose features are not illustrated. The trapping laser 160 can also be directed into the microsystem 110 via the microscope.

In an alternative design of the device according to the invention, the structured masks are directly implemented on the light sensitive surface of the detector. Furthermore, it can be provided that the detector is not formed by a single photodiode, but by a CCD matrix. In this type of design, imaging of the locational area of the particle on the CCD matrix and subsequent electronic masking of the matrix signal through evaluation of the signals from specific image points can be performed.

What is claimed is:

1. A process for object detection, comprising the steps:
    enlarged optical imaging of at least one resting or moving object with a microscope onto a structured mask being positioned in a beam path of the microscope and having at least one segment adapted for transmitting light from a flat section to a detector unit, wherein said object is located at least partially or temporarily in said flat section, and said flat section has a characteristic dimension smaller than a dimension of the object or a movement path of the object;
    detecting a quantity of light transmitted by the structured mask;
    generating a detector signal having a predetermined relationship with the quantity of light; and
    evaluating the detector signal in regard to at least one of a presence of the object, a position of the object, a shape of the object, and a temporal change of the position of the object.

2. The process according to claim 1, wherein the object comprises synthetic or biological particles in a microchannel of a fluidic microsystem, wherein the particles are subjected to at least one of hydrodynamic, acoustic, magnetic and electrical forces.

3. The process according to claim 2, wherein the structured mask is positioned in relation to the fluidic microsystem in such a way that light is transmitted by the structured mask from a section in which the particles are to be positioned or moved.

4. The process according to claim 2, wherein the structured mask is positioned in relation to the fluidic microsystem in such a way that light is transmitted by the structured mask from a section into which the particles are not to enter.

5. The process according to claim 2, wherein the particles as fixed or moved with a trapping laser.

6. The process according to claim 5, wherein the particles are brought into contact with a modification layer, a cell, or receptors in the fluidic microsystem with the trapping laser and, during the evaluation of the detector signal in regard to movement characteristics of the particles, parameters are determined which are characteristic for interaction of the particles with the modification layer, the cell, or the receptors.

7. The process according to claim 1, further comprising at least one of the following additional steps:
    detecting a presence of a resting particle by detecting whether the detector signal has a predetermined, unchanging amplitude;
    detecting a presence of a moving particle at a specific position by determining whether the detector signal has a predetermined time characteristic;
    detecting frequencies and speeds of particles by evaluating maxima of the detector signal in regard to width and interval of the maxima; and
    counting particles by counting the maxima of the detector signal.

8. The process according to claim 7, further comprising at least one of determining a direction of particle movement, and size-dependent counting of particles.

9. The process according to claim 1, further comprising at least one of evaluating an amplitude of the detector signal, and evaluating a variability of the detector signal.

10. The process of claim 1, further comprising at least one of: (a) dielectric single particle spectroscopy in fluidic microsystems; (b) measurement of electromagnetic forces in microelectrode arrangements; (c) measurement of optical forces in trapping lasers; (d) detection of the function of microelectrodes in microsystems; (e) detection of at least one of particle positions, particle movements, particle numbers, and particle interactions; and (f) measurement of particle rotations induced by rotating electrical fields.

11. A device for object detection, which comprises:

an optical imaging unit for enlarged imaging of at least one resting or moving object with a microscope onto a structured mask positioned in a beam path of the microscope, having at least one light transmitting segment adapted to transmit light from a flat section to a detector unit, wherein the object is located at least partially or temporarily in the flat section and the flat section has a characteristic dimension smaller than a dimension of the object or a movement path of the object;

a detector unit for detecting a quantity of light transmitted by the structured mask and for forming a detector signal having a predetermined relationship with the quantity of light; and an evaluation unit for evaluation of tie detector signal in regard to at least one of a presence of the object, a position of the object, a shape of the object and a temporal change of the position.

12. The device according to 11, wherein the structured mask is a transmission screen with at least one transparent segment.

13. The device according to claim 12, wherein multiple segments are prided which are positioned two-dimensionally in a plane of the structure mask.

14. The device according to claim 12, wherein at least one cross-shaped segment, frame-shaped segment, straight-shaped segment and curved strip-shaped segments is provided.

15. The device according to claim 11, wherein the detector unit is adapted for integrated detection of a partial image of the object or a movement path of the object transmitted or reflected by the structured mask.

16. The device according to claim 11, adapted for object detection of synthetic or natural particles in a fluidic microsystem.

17. The device according to claim 16, wherein the particles in the fluidic microsystem are subjected to at least one of hydrodynamic, acoustic, magnetic and electrical forces.

18. The device according to claim 16, wherein a trapping laser arrangement is provided for manipulation of the particles in the fluidic microsystem.

19. The device according to claim 11, wherein the light transmitting segment has a characteristic dimension smaller than the object or a movement path of the object, or is smaller than an image of the object or a movement path of the image.

20. A process for object detection, with the steps:

optical imaging of at least one resting or moving object on a CCD matrix detector;

electronic masking of a signal of said CCD matrix detector for providing signals from specific image points of said object; and evaluating said signals from specific image points in regard to at least one of a presence of the object, a position of the object, a shape of the object and a temporal change of the position.

* * * * *